United States Patent
Schmid et al.

[11] Patent Number: 6,063,179
[45] Date of Patent: May 16, 2000

[54] GONIOCHROMATIC GLOSS PIGMENTS BASED ON COATED SILICON DIOXIDE PLATELETS

[75] Inventors: Raimund Schmid, Neustadt; Norbert Mronga, Dossenheim, both of Germany

[73] Assignee: BASF Aktiengesellschaft, Ludwigshafen, Germany

[21] Appl. No.: 09/147,123

[22] PCT Filed: Apr. 3, 1997

[86] PCT No.: PCT/EP97/01674

§ 371 Date: Oct. 13, 1998

§ 102(e) Date: Oct. 13, 1998

[87] PCT Pub. No.: WO97/39066

PCT Pub. Date: Oct. 23, 1997

[30] Foreign Application Priority Data

Apr. 13, 1996 [DE] Germany .......................... 196 14 637

[51] Int. Cl.[7] .................................................. C09C 1/28
[52] U.S. Cl. .................. 106/415; 106/437; 106/446; 106/481; 106/482; 427/585; 427/215; 427/255; 427/255.7; 427/377
[58] Field of Search ............................ 428/404; 427/585, 427/215, 255.7, 255, 377; 106/415, 437, 446, 481, 482

[56] References Cited

U.S. PATENT DOCUMENTS 5,763,086 6/1998 Schmid et al. ..................... 428/404

FOREIGN PATENT DOCUMENTS

| | | |
|---|---|---|
| 0 045 851 | 7/1981 | European Pat. Off. . |
| 0 338 428 | 4/1989 | European Pat. Off. . |
| 0 579 091 | of 1993 | European Pat. Off. . |
| 0 668 329 | 2/1995 | European Pat. Off. . |
| 0 641 842 | 3/1995 | European Pat. Off. . |
| 0 678 561 | 4/1995 | European Pat. Off. . |
| 41 40 900 | 12/1991 | Germany . |
| 42 36 332 | 10/1992 | Germany . |
| 43 19 669 | 1/1994 | Germany . |
| 44 03 678 | 2/1994 | Germany . |
| 195 16 181 | 5/1995 | Germany . |
| 44 41 223 | 6/1995 | Germany . |
| WO 93/08237 | 4/1993 | WIPO . |
| WO 93/8237 | 4/1993 | WIPO . |
| WO 93 12182 | 6/1993 | WIPO . |

OTHER PUBLICATIONS

Chemical Abstract citation 123:259,909: abstract for DE 4,441,223, Jun. 1, 1995.
Chemical Abstract citation 120:10,430: abstract for WO 93/8237, Apr. 29, 1993.
Proceedings of the XIVTH International Conference in Organic Coatings Science and Technology, vol. 12, Angelos V. Patsis, Jul. 11–15, 1998, Technomic Publishing Co., Inc.

*Primary Examiner*—C. Melissa Koslow
*Attorney, Agent, or Firm*—Oblon, Spivak, McClelland, Maier & Neustadt, P.C.

[57] ABSTRACT

Goniochromatic luster pigments based on silicon dioxide platlets, CVD coated with A) a nonselectively absorbing filmlike layer at least partially transparent to visible light, and B) if desired an outer layer which consists essentially of colorless or selectively absorbing metal oxide and/or comprises phosphate, chromate and/or vanadate, are prepared and used for coloring paints, inks, including printing inks, plastics, glasses, ceramic products and decorative cosmetic preparations.

13 Claims, No Drawings

GONIOCHROMATIC GLOSS PIGMENTS BASED ON COATED SILICON DIOXIDE PLATELETS

SPECIFICATION

The present invention relates to novel goniochromatic luster pigments based on silicon dioxide platelets, CVD coated with A) a nonselectively absorbing filmlike layer at least partially transparent to visible light, and B) if desired an outer layer which consists essentially of colorless or selectively absorbing metal oxide and/or comprises phosphate, chromate and/or vanadate.

This invention further relates to the production of these luster pigments and to their use for coloring paints, inks, including printing inks, plastics, glasses, ceramic products and decorative cosmetic preparations.

Luster effect pigments are used in many sectors of industry, for example in automotive coatings, decorative coating, plastics pigmentation, paints, printing inks, especially security printing inks, and cosmetics.

Their optical effect is based on the directed reflection of light at predominantly sheetlike, mutually parallel-oriented, metallic or strongly refractive pigment particles. Depending on the composition of the pigment platelets, interference, reflection and absorption phenomena create angle-dependent color and lightness effects.

Owing to their uncopyable optical effects, these pigments are becoming increasingly important for the production of forgeryproof security documents, such as banknotes, checks, checkcards, credit cards, tax stamps, postage stamps, rail and air tickets, telephone cards, lottery tickets, gift vouchers, passes and identity cards.

Markings prepared using luster effect pigments and the absence of these markings or their alteration, for example in a color copy (disappearance of color flops and luster effects), are reliably discernible by the unaided, naked eye and so make it easy to distinguish the copy from the original.

WO-A-93/08237 discloses luster pigments based on platelet-shaped substrate particles composed of a silicon dioxide matrix, wet-chemically coated with metal oxides by hydrolysis of metal salts or with metals by reduction of aqueous metal salts. The substrate $SiO_2$ platelets are produced by brushing a waterglass solution on a circulating belt in a thickness of about 10 $\mu$m, drying and then washing the waterglass film initially with acid and then with water, detaching the resulting gellike $SiO_2$ film and washing and also grinding the resulting fragments. The $SiO_2$ platelets can also be colored by incorporating colorants in the waterglass film.

However, the metal-coated $SiO_2$ platelet luster pigments described in WO-A-93/08237 are not satisfactory, since the wet-chemical metalization fails to produce an unbroken metal film, but deposits the metal in a more coarsely crystalline, island like state. Hence the exemplified coating of the $SiO_2$ platelets with silver produces only silvery gray platelets which do not exhibit any interference colors.

Similarly, the physical vapor deposition (PVD) process mentioned therein fails to produce metalized $SiO_2$ platelets in satisfactory quality. To obtain $SiO_2$ platelets that are metalized on both sides, the circulating belt would initially have to have a metal film vapor-deposited onto it in a vacuum chamber. The thus-coated belt would then have to be passed through the waterglass solution. In the course of this step and in the course of the subsequent acidic wash of the silicate film, the metal film would be attacked. Also, the $SiO_2$ film will crumble off the belt during the wash, making it difficult to vapor-deposit the second metal layer.

It is an object of the present invention to provide goniochromatic luster pigments having good coloristic and application properties.

We have found that this object is achieved by the luster pigments defined at the beginning.

The present invention further provides a process for producing these luster pigments, which comprises coating silicon dioxide platelets with said layer (A) and if desired said layer (B) by chemical gas phase decomposition of vaporizable metal compounds.

This invention also provides for the use of these luster pigments for coloring paints, inks, including printing inks, plastics, glasses, ceramic products and decorative cosmetic preparations.

In the luster pigments of the present invention, $SiO_2$ platelets are CVD coated with a nonselectively absorbing filmlike layer (A) at least partially transparent to visible light and, if desired, with a colorless or selectively absorbing layer (B) which is likewise produced from the gas phase and comprises metal oxide and/or phosphate, chromate and/or vanadate.

Coatings (A) and (B) applied according to the invention are notable for their high quality. They have a homogeneous and filmlike construction, completely enrobe the $SiO_2$ particles and cover not just the platelet surface and subface, and produce luster pigments having strong interference colors and highly angle-dependent color interplay.

The $SiO_2$ platelets functioning as substrate in the luster pigments of the invention may be obtained as described in WO-A-93/08237. Their diameter is customarily within the range from 1 to 250 $\mu$m, preferably within the range from 2 to 100 $\mu$m, and their thickness is generally within the range from 0.05 to 5 $\mu$m, especially within the range from 0.2 to 2 $\mu$m.

The $SiO_2$ platelets may be colored by the incorporation of inorganic or organic colorants. The term "inorganic colorants" is in this context to be understood as meaning inorganic pigments in a very finely divided form which are incorporated in the $SiO_2$ matrix as solid particles, or colored metal cations with which the matrix is doped. Organic colorants may be organic pigments or dyes. Preferably, however, the $SiO_2$ platelets are not colored.

Furthermore, the $SiO_2$ platelets may already be coated with a colorless, highly refractive metal oxide. Here preference is given to titanium dioxide, which is customarily applied in a layer from 5 to 200 nm in thickness.

The nonselectively absorbing layer (A) is preferably constructed from metals and/or nonselectively absorbing metal compounds.

Suitable metal compounds include black metal sulfides, metal oxides, metal nitrides and metal silicides.

Examples of preferred layer materials (A) are iron, cobalt, nickel, chromium, molybdenum, tungsten, aluminum, silicon, iron sulfide, cobalt sulfide, nickel sulfide, chromium sulfide, molybdenum sulfide, tungsten sulfide, magnetite, cobalt oxide, nickel oxide, iron nitride, cobalt nitride, nickel nitride, chromium nitride, molybdenum nitride, tungsten nitride, iron silicide, chromium silicide, molybdenum silicide and tungsten silicide, of which iron, molybdenum, aluminum, molybdenum sulfide, magnetite and molybdenum silicide are particularly preferred.

Particularly suitable mixtures are, for example, iron and magnetite, molybdenum and molybdenum sulfide, iron and iron sulfide, and also molybdenum and chromium.

The black layer (A) should self-evidently not be opaque, but must be at least partially transparent to visible light, i.e., should transmit in general not less than 10%, preferably not less than 30%, of incident light.

Depending on the optical properties of the layer material (A), the layer thickness is generally within the range from 1 to 50 nm. In the case of strongly absorbing, high refractive materials such as molybdenum, chromium, aluminum, molybdenum sulfide and molybdenum silicide preferred layer thicknesses are generally up to 20 or 25 nm, whereas the layer thickness for less strongly absorbing or low refractive materials such as magnetite and silicon is preferably within the range from 10 to 50 nm and from 20 to 30 nm, respectively.

The $SiO_2$ platelets coated with the black, semitransparent layer (A) show intensive interference colors, which are determined by the thickness of the $SiO_2$ platelets and also by the thickness of any $TiO_2$ coating present, and also conspicuous hue changes with varying angles of observation or illumination.

The luster pigments of the invention may additionally have an outer layer (B), which particularly serves to protect metallic layers (A), but may also contribute to the interference of the pigment and continue the interference series at the location determined by the substrate coated with (A) [high refractive layer materials (B)]. Color layers (B) modify the interference colors of the pigment by adding their absorption color and finally cover it over with increasing layer thickness.

Suitable layers (B) are layers consisting essentially of colorless or selectively absorbing metal oxides, which may be low or high refractive, or layers which comprise phosphate, chromate and/or vanadate and are obtainable by gas phase passivation, and also layers comprising phosphate and silicon dioxide.

Examples of preferred metal oxides (B) are silicon dioxide, aluminum oxide, tin dioxide, titanium dioxide, zirconium dioxide, iron(III) oxide and chromium(III) oxide.

The thickness of layer (B) is generally within the range from 1 to 400 nm, preferably within the range from 5 to 250 nm. Optimal layer thickness depends on the optical and/or passivating properties of the individual layer material. For instance, the preferred thickness for $SiO_2$ layers (B) is within the range from 5 to 250 nm, for $TiO_2$ and $ZrO_2$ layers (B) within the range of up to 100 nm, for $Fe_2O_3$ and $Cr_2O_3$ layers (B), for $Al_2O_3$ layers (B) formed by anodization of aluminum layers (A) and for phosphate- and $SiO_2$-comprising layers (B) within the range of 5 to 20 nm.

In the inventive process for producing the novel luster pigments, the layers (A) and if desired (B) are applied from the gas phase (CVD) by chemical decomposition of suitable starter compounds of the metals to the $SiO_2$ platelets, which may already have a first, high refractive metal oxide layer.

The gas phase coating is preferably carried out in a heatable fluidized bed reactor as described, for example, in EP-A-45 851, where the substrate particles are initially fluidized with a gas and heated to the temperature, generally within the range from 100 to 600° C., necessary to decompose the respective metal compound. The metal compounds vaporized in an upstream vaporizer vessel using a suitable carrier gas and also any gases required for decomposition are then introduced via separate nozzles.

However, the reactor used can also be a single-neck round-bottom flask made of quartz glass which is rotated by a motor, provided with gas inlet and outlet lines in the axis of rotation and heated by a clamshell oven (rotary sphere oven).

In principle the reactor used can be any heatable mixer which agitates the substrate particles gently by means of appropriate internal fitments and permits the supply and removal of gas.

For a continuous process on an industrial scale it is also possible to use, for example, a rotary tube furnace to which a mixture of substrate particles and the gas mixture are fed continuously.

Metallic layers (A) are preferably applied in the process of the invention by inert gas phase decomposition of metal carbonyls (at from 50 to 400° C., preferably at from 70 to 350° C.), organometals (at from 100 to 500° C., preferably at from 150 to 400° C.) and metal hydrides (at from 100 to 600° C., preferably at from 150 to 500° C.).

Specific examples of particularly suitable metal compounds are:

metal carbonyls such as iron pentacarbonyl, chromium hexacarbonyl, molybdenum hexacarbonyl, tungsten hexacarbonyl, nickel tetracarbonyl and dicobalt octacarbonyl (WO-A-93/12182);

organometallics, especially aluminum alkyls such as triethylaluminum and trimethylaluminum (DE-A-19516181, unpublished at the priority date of the present invention);

metal hydrides, especially silicon hydrides such as monosilane ($SiH_4$), trisilane ($Si_3H_8$) and disilane ($Si_2H_6$) (prior German patent application 19538295.1).

Mixed metal layers (A) (e.g., those of essentially molybdenum and chromium) can be applied by simultaneous or by successive decomposition of the carbonyls, in which case, especially for thin layers (B), the second variant is to be preferred, since thorough mixing of the deposited layers takes place.

Metal silicide layers (A), which may include the elemental metal and silicon as well as the metal silicide, are advantageously obtained by simultaneous decomposition of silanes and metal carbonyls (e.g., molybdenum hexacarbonyl).

Metal sulfide layers (A), which, depending on their method of production, may include the elemental metal or an oxide of the metal as well as the metal sulfide, can be applied by both the process variants described in EP-A-579 091, either by gas phase decomposition of metal carbonyls in the presence of an inert gas or oxygen and/or water vapor to initially deposit a metal or metal oxide layer which is then reacted with a volatile sulfur compound (preferably hydrogen sulfide) or with sulfur vapor to convert it into the desired metal sulfide layer (A), or directly by gas phase decomposition of volatile metal compounds in a sulfur atmosphere. Suitable reaction temperatures are generally within the range from 200 to 500° C., preferably within the range from 300 to 450° C.

Metal nitride layers (A) may with advantage be deposited by decomposition of the metal carbonyls in the presence of ammonia at a temperature which is generally within the range from 100 to 600° C., especially within the range from 150 to 400° C. (EP-A-690 105).

Nonselectively absorbing metal oxide layers (A) are especially obtained by decomposition of the metal carbonyls in the presence of water vapor (lower metal oxides such as magnetite) or in the presence of oxygen and if desired water vapor (e.g., nickel oxide and cobalt oxide).

Outer layers (B) composed of metal oxides can be applied in the process of the present invention by oxidative gas phase decomposition of the metal carbonyls (e.g., iron pentacarbonyl, chromium hexacarbonyl; EP-A-45 851), by hydrolytic gas phase decomposition of the metal alkoxides (e.g., titanium and zirconium tetra-n-pro-poxide and -isopropoxide; DE-A-41 40 900) or of the metal halides (e.g., titanium tetrachloride; EP-A-338 428), by oxidative decomposition of organotin compounds (especially tin alkyls such as tin tetrabutyl and tin tetramethyl; DE-A-44 03 678) or by the gas phase hydrolysis, described in EP-A-668 329, of organosilicon compounds (especially by the gas phase hydrolysis of di-tert-bu-toxyacetoxysilane).

$Al_2O_3$ layers (B) can with advantage be obtained by controlled oxidation in the course of the cooling—otherwise carried out under inert gas—of the pigments coated with aluminum (A) (DE-A-19516181, unpublished at the priority date of the present invention).

Phosphate-, chromate- and/or vanadate-comprising and also phosphate- and $SiO_2$-comprising outer layers (B) can be applied by the passivation processes described in DE-A-42 36 332 and EP-A678 561 by hydrolytic or oxidative gas phase decomposition of oxyhalides of the metals (e.g., $CrO_2Cl_2$, $VOCl_3$), especially of phosphorus oxyhalides (e.g., $POCl_3$), phosphoric and phosphorous esters (e.g., di- and trimethyl and -ethyl phosphite) and of amino-containing organosilicon compounds (e.g., 3-aminopropyltriethoxysilane and 3-aminopropyltrimethoxysilane).

The combined decomposition of phosphorus and silicon compounds produces luster pigments having a metallic layer (A) which are particularly stable in aqueous systems.

The production process of the present invention makes it possible to produce the multiply coated luster pigments reproducibly in large quantities in a simple manner. The pigment particles obtained are completely enrobed and have individual coatings of high quality (homogeneous, filmlike).

The luster pigments of the present invention are advantageously useful for many purposes, such as the coloring of plastics, glasses, ceramic products, decorative cosmetic preparations and in particular coatings, especially automotive coatings, and inks, especially security printing inks. All customary printing processes can be employed, for example screen printing, intaglio printing, bronze printing, flexographic printing and offset printing.

The pigments of the present invention are also advantageously useful for these purposes in admixture with transparent and hiding white, color and black pigments and also conventional transparent, colored and black luster pigments based on metal oxide-coated mica and metal pigments, platelet-shaped iron oxides, graphite, molybdenum sulfide and platelet-shaped organic pigments.

We claim:

1. A goniochromatic luster pigment based on silicon dioxide platelets, CVD coated with:
    A) a nonselectively absorbing film layer at least partially transparent to visible light;
    B) Optionally an outer layer which comprises colorless or selectively absorbing metal oxides, phosphates, chromates or vanadates or any combination thereof;
    wherein the silicon dioxide platelets are already coated with an inner, colorless, reflective metal oxide layer.

2. The luster pigment of claim 1, wherein said layer (A) comprises metals of nonselectively absorbing metal compounds or mixtures thereof.

3. The luster pigment of claim 2, wherein said nonselectively absorbing compounds comprise metal sulfides, metal oxides, metal nitrides or metal silicides or any combination thereof.

4. The luster pigment of claim 1, wherein the silicon dioxide platelets are colored by incorporation of inorganic or organic colorants.

5. The luster pigment of claim 1, wherein said layer (A) is from 1 to 50 nm in thickness.

6. The luster pigment of claim 1, wherein said layer (B) is from 1 to 400 nm in thickness.

7. The luster pigment of claim 1, wherein said film layer (A) completely enrobes the silicon dioxide platelets.

8. The luster pigment of claim 1, wherein said silicon dioxide platelets have a diameter of from 1 to 250 μm.

9. The luster pigment of claim 8, wherein said silicon dioxide platelets have a diameter of from 0.05 to 5 μm.

10. The luster pigment of claim 9, wherein said silicon dioxide platelets have a diameter of from 0.2 to 2 μm.

11. The luster pigment of claim 1, wherein said color, reflective metal oxide layer comprises titanium dioxide having a thickness of from 5 to 200 nm.

12. A process for producing the luster pigment of claim 1, which comprises coating silicon dioxide platelets with a nonselectively adsorbing film layer at least partially transparent to visible light by chemical gas phase decomposition of vaporizable metal compounds.

13. The process of claim 12, which further comprises coating said silicon dioxide platelets with an outer layer which comprises metal oxides, sulfates, chromates or vanadates or any combination thereof.

* * * * *